US006834650B1

United States Patent
Fini et al.

(10) Patent No.: US 6,834,650 B1
(45) Date of Patent: Dec. 28, 2004

(54) FACE OR NOSE MASK FOR NON-INVASIVE VENTILATION OF PATIENTS IN GENERAL

(75) Inventors: Massimo Fini, Mirandola (IT); Paolo Bergamaschi, Concordia (IT); Stefano Nava, Crema (IT)

(73) Assignee: Mallinckrodt, Inc., Hazelwood, MO (US)

( * ) Notice: Subject to any disclaimer, the term of this patent is extended or adjusted under 35 U.S.C. 154(b) by 0 days.

(21) Appl. No.: 10/018,899

(22) PCT Filed: Mar. 9, 2000

(86) PCT No.: PCT/US00/06164

§ 371 (c)(1),
(2), (4) Date: Jun. 6, 2002

(87) PCT Pub. No.: WO00/53265

PCT Pub. Date: Sep. 14, 2000

(30) Foreign Application Priority Data

Mar. 12, 1999 (IT) .......................... MI99A0521

(51) Int. Cl.[7] .............................................. A62B 18/08
(52) U.S. Cl. ............................ 128/206.26; 128/206.24; 128/205.25

(58) Field of Search ...................... 128/206.23, 206.24, 128/206.26, 205.25

(56) References Cited

U.S. PATENT DOCUMENTS

| | | | | | |
|---|---|---|---|---|---|
| 2,047,216 | A | * | 7/1936 | McKesson | 128/202.23 |
| 2,749,910 | A | * | 6/1956 | Faulconer, Jr. | 601/44 |
| 2,875,757 | A | * | 3/1959 | Galleher, Jr. | 128/206.26 |
| 3,330,273 | A | * | 7/1967 | Bennett | 128/206.26 |
| 3,330,274 | A | * | 7/1967 | Bennett | 128/206.26 |
| 4,799,477 | A | * | 1/1989 | Lewis | 128/206.24 |
| 4,971,051 | A | * | 11/1990 | Toffolon | 128/206.26 |
| 5,560,354 | A | * | 10/1996 | Berthon-Jones et al. | 128/205.25 |
| 5,660,174 | A | * | 8/1997 | Jacobelli | 128/206.24 |

* cited by examiner

Primary Examiner—Henry Bennett
Assistant Examiner—Mital Patel
(74) Attorney, Agent, or Firm—Fulwider Patton Lee & Utecht, LLP

(57) ABSTRACT

The face or nose mask (1) includes a mask body (2) with an inlet (3). The mask body (2) includes a sealing element with a first chamber (10), and a second chamber (11) which can be connected by connectors (12, 13) to a source of pressurized air.

3 Claims, 1 Drawing Sheet

FACE OR NOSE MASK FOR NON-INVASIVE VENTILATION OF PATIENTS IN GENERAL

RELATED APPLICATIONS

Figure 1:
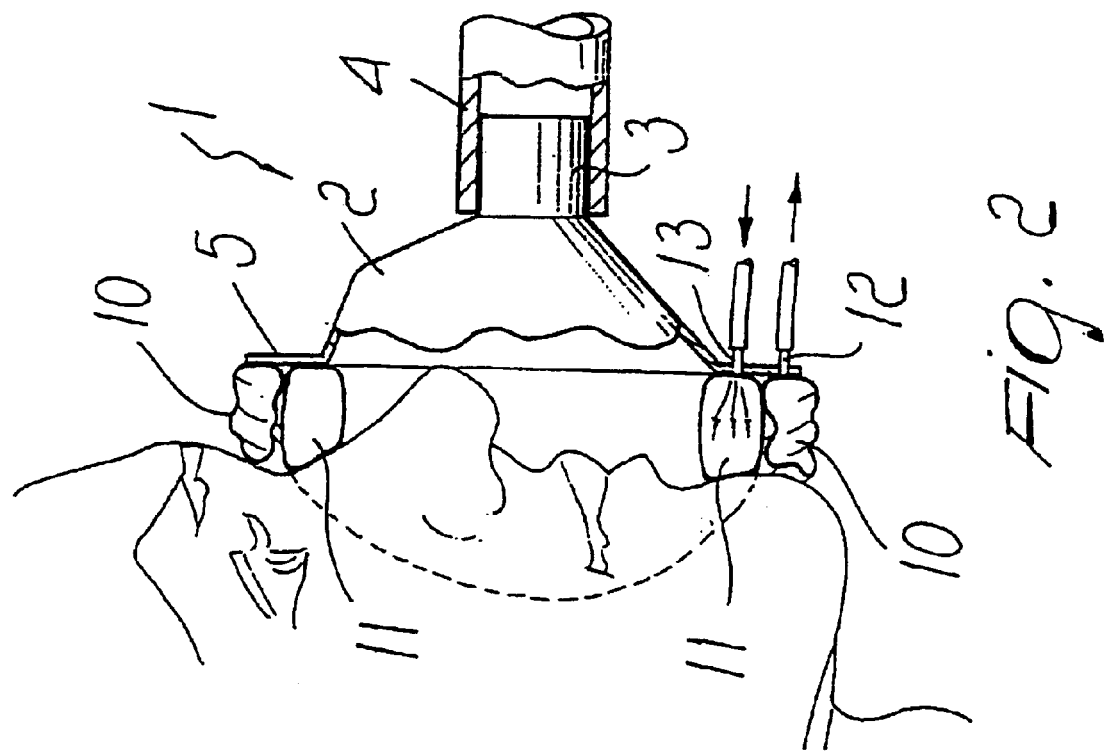

This application claims priority from PCT International Application No. PCT/US00/06164, having the international filing date of 9 Mar. 2000, and Italian Application No. MI 99A000521, filed Mar. 12, 1999.

The present invention relates to a face or nose mask for non-invasive ventilation of patients in general.

It is known that the main problem in long-term ventilation performed by means of a mask is the tolerability of the mask by the patient.

One of the most unpleasant and harmful effects arises from the compression of the skin that is produced by the sealing element provided in the perimetric region of the mask, which is pressed against the user's face; this effect is particularly damaging at the upper nasal region.

The pressure applied by the mask in fact reduces blood flow in the affected part of the skin and in the long term causes pain and sores may form in the region.

In order to try to at least partially solve this problem, masks have already been provided in which the sealing element is formed in practice by an air-filled chamber or air cushion which, in order to reduce the period of contact with the skin, is in practice deflated at least at the upper part of the nasal septum during expiration, a step in which there is no need to provide a seal since the patient is expelling air. The chamber is then instantly reinflated during inspiration, thus forming a seal again and in practice reducing the time of contact between the skin and the inflatable chamber.

Also this solution has not proved to be particularly effective, since the inflation and deflation rate is closely dependent on the ratio between the expiration phase and the inspiration phase and because a relatively high residual pressure always remains and is applied by the mask to the skin.

The aim of the present invention is to eliminate the above-noted drawbacks, by providing a face or nose mask for non-invasive ventilation of patients in general which allows to reduce the time for which the pressure produced by the sealing element of the mask is applied, so that the above-mentioned problems do not occur since blood flow in the affected skin portion is possible at all times. Within the scope of this aim, a particular object of the present invention is to provide a face or nose mask in which the perfect seal of the mask with respect to the outside is ensured at all times but the region where pressure is applied to the skin changes continuously.

Another object of the present invention is to provide a mask in which the system for inflating the sealing element is independent of the ventilation system, consequently allowing a wide range of adjustment for the pressure values used.

Another object of the present invention is to provide a mask which, by way of its particular constructive characteristics, is capable of giving the greatest assurances of reliability and safety in use.

Another object of the present invention is to provide a face or nose mask for non-invasive ventilation of patients in general which can be easily obtained starting from commonly commercially available elements and materials and is also competitive from a purely economical point of view.

This aim, these objects and others which will become apparent hereinafter are achieved by a face or nose mask for non-invasive ventilation of patients in general, according to the invention, which comprises a mask body provided with an inlet for connection to a ventilation apparatus and perimetrically provided with a sealing element for application to the face of a patient, characterized in that said sealing element comprises at least one first chamber and at least one second chamber which can be connected separately to a source of pressurized air.

Figure 2:
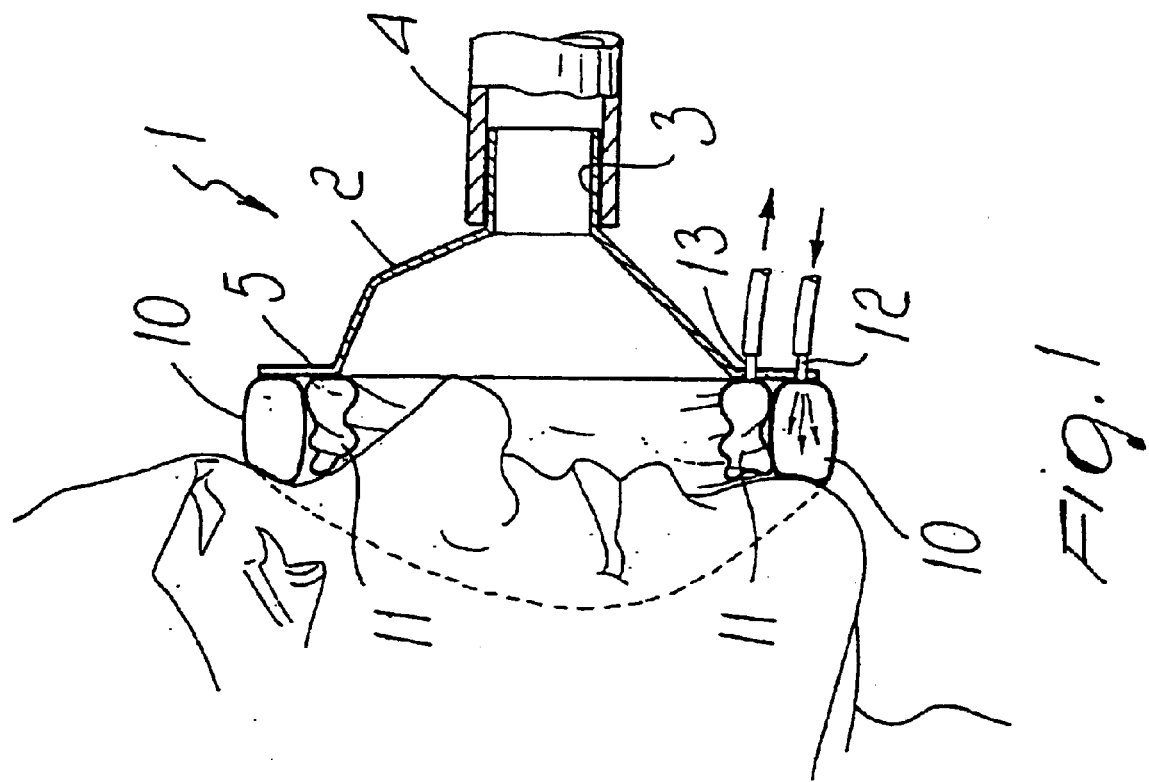

Further characteristics and advantages of the present invention will become apparent from the following detailed description of a preferred but not exclusive embodiment of a face or nose mask for non-invasive ventilation of patients in general, illustrated only by way of non-limitative example in the accompanying drawings, wherein:

FIG. 1 is a partially sectional schematic view of the mask according to the invention with the seal provided by one chamber; and FIG. 2 is a view of the mask with the seal produced by the other chamber.

With reference to the above figures, the face or nose mask for non-invasive ventilation of patients in general, according to the invention, generally designated by the reference numeral 1, comprises a mask body 2 which has the conventional configuration of a face or nose mask and is provided with an inlet 3 for connection, by means of a hose 4, to a ventilation apparatus.

In the perimetric region, the mask has a flange 5 at which the sealing element for application to the face of the patient is provided.

The particularity of the invention is constituted by the fact that the sealing element is provided by at least one first chamber 10 and by at least one second chamber 11 which are advantageously arranged side by side, the first chamber being arranged outside with respect to the second chamber.

The chambers have separate connections to a source of pressurized air, and in particular there is provided a first connector 12 for the first chamber and a second connector 13 for the second chamber 11; such connectors are connected to an inflation device which is constituted for example by extremely compact micropumps which can be actuated sequentially so as to release the pressure in one chamber and inflate the other chamber, thus ensuring the seal.

The inflation and deflation rate can be adjusted in any manner, since it is independent of the ventilator of the ventilation system.

In practice it is possible to alternate inflation and deflation with a period of a few seconds, consequently having the advantage that the skin is affected in the same region for a period which is substantially halved, but most of all with the advantage that in practice blood flow is never interrupted or hindered, thus preventing the occurrence of pain and dangerous sores.

In practice, the system adopted consists in removing pressure from one chamber and simultaneously restoring pressure in the other chamber, so that the seal is ensured at all times but the region where pressure is applied to the skin changes.

Advantageously, the chambers have a closed perimeter, but from the conceptual point of view there is no difference if the chambers 10, 11 affect only portions of the face and in any case the regions that are more severely affected by pain or sores, depending on the pressure applied in order to provide the seal.

From the above description it is thus evident that the invention achieves the intended aim and objects, and in particular the fact is stressed that a face mask is provided which has an inflatable sealing element which is entirely autonomous and independent of the ventilator used for ventilation, thus allowing to adjust the pressure inside the individual chambers independently of each other and to provide alternating deflation and inflation of the chambers at a rate which can be adjusted at will in view of the fact that the chambers are separately connected to a source of pressurized air, for example constituted by micropumps.

The invention thus conceived is susceptible of numerous modifications and variations, all of which are within the scope of the inventive concept All the details may also be replaced with other technically equivalent elements.

In practice, the materials employed, as well as the contingent shapes and the dimensions, may be any according to requirements.

What is claimed is:

1. In a face or nose mask for non-invasive ventilation of patients in general, comprising a mask body provided with an inlet for connection to a ventilation apparatus and perimetrically provided with a sealing element for application to the face of a patient, the improvement in said face or nose mask wherein said sealing element comprises at least one first inflatable chamber and at least one second inflatable chamber, said at least one first inflatable chamber having a first connector connectable to a source of pressurized air, and said at least one second inflatable chamber having a second connector connectable to the source of pressurized air, said second inflatable chamber capable of being inflated separately from said first chamber, and said first and second inflatable chambers being alternatingly inflated and deflated seguentially independently of ventilation provided by the ventilation apparatus.

2. The mask according to claim 1, wherein said first and second inflatable chambers have a closed perimeter.

3. The mask according to claim 1, wherein said first and second inflatable chambers lie concentrically side by side.

* * * * *

UNITED STATES PATENT AND TRADEMARK OFFICE
CERTIFICATE OF CORRECTION

PATENT NO. : 6,834,650 B1
DATED : December 28, 2004
INVENTOR(S) : Massimo Fini et al.

It is certified that error appears in the above-identified patent and that said Letters Patent is hereby corrected as shown below:

Column 1,
Line 45, after "times." add new paragraph before "Within".

Column 2,
Line 38, delete "chamber" and insert -- chamber 10 --.

Column 3,
Line 12, delete "concept" and insert -- concept. --.
Line 12, after "concept." add new paragraph before "All".

Column 4,
Line 11, delete "chamber,and" and insert -- chamber, and --.
Line 13, delete "seguentially" and insert -- sequentially --.

Signed and Sealed this

Tenth Day of May, 2005

JON W. DUDAS
*Director of the United States Patent and Trademark Office*